United States Patent
Horiuchi

[11] Patent Number: 6,139,552
[45] Date of Patent: Oct. 31, 2000

[54] BONE JOINTER AND A BONE JOINTER FIXING TOOL

[75] Inventor: Kikuji Horiuchi, Numazu, Japan

[73] Assignee: K. K. Hollyx, Shizuoka, Japan

[21] Appl. No.: 09/310,731

[22] Filed: May 13, 1999

[30] Foreign Application Priority Data

May 13, 1998 [JP] Japan .................................. 10-129371
Mar. 19, 1999 [JP] Japan .................................. 11-075353

[51] Int. Cl.$^7$ .................................................. A61B 17/58
[52] U.S. Cl. .............................................. 606/88; 606/65
[58] Field of Search ................................. 606/88, 60, 65, 606/66, 67, 68, 70, 72, 73, 87

[56] References Cited

U.S. PATENT DOCUMENTS 5,797,913  8/1998  Dambreville et al. ..................... 606/72
5,871,485  2/1999  Rao et al. ................................. 606/65

FOREIGN PATENT DOCUMENTS 3044923  10/1997  Japan ........................................ 606/88

*Primary Examiner*—Michael Buiz
*Assistant Examiner*—Lien Ngo
*Attorney, Agent, or Firm*—McGinn & Gibb, P.C.

[57] ABSTRACT

A bone jointer comprising a lag screw, a tube placed along the jointed bone and provided with a receiving part, a tube between the lag screw and the tube plate provided with a head to be movably engaged with the receiving part, a set screw engaged with the tube, a compression screw penetrating inside the set screw and engaged with the lag screw thereby the lag screw and the bone are drew toward the other bone, and a washer between the set screw and the receiving part, rotating during engagement of the set screw with the head, until the washer stops at a stablest position.

Further, a bone jointer fixing tool comprising a plate provided with a receiving part having a penetration hole, a screw having a shaft and a head in slidable contact with the penetration hole of the receiving part and also having another penetration hole for drilling, a washer in slidable contact with the penetration hole of the receiving part, and a fastening part engaged with the screw and having a penetration hole for drilling, wherein, while the screw is engaged with the fastening part in arbitrary direction, the washer rotates and stops at the stablest position, thereby the screw and the fastening part are engaged with each other by maintaining the arbitrary direction.

5 Claims, 20 Drawing Sheets

FIG. 9
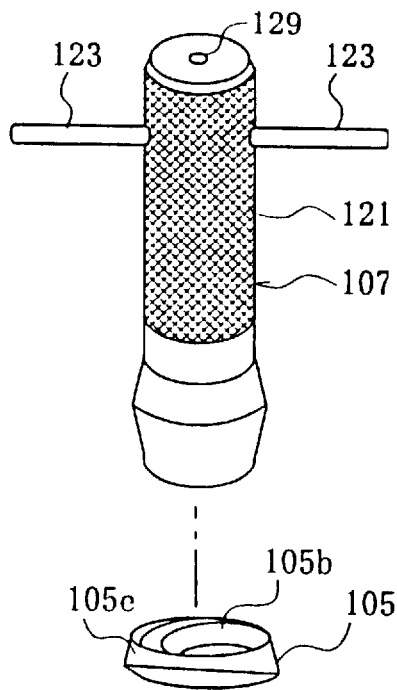
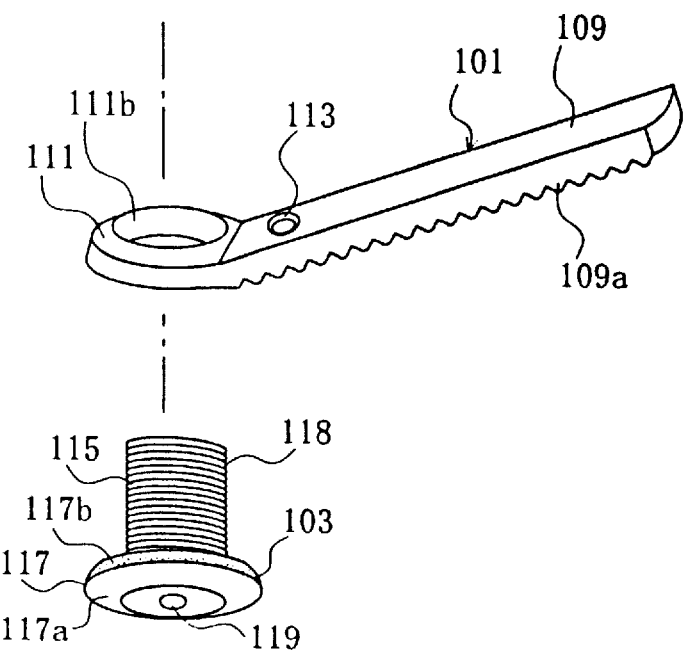

F I G. 1 2
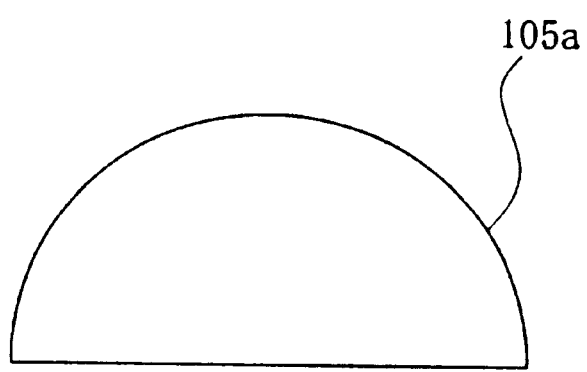

BONE JOINTER AND A BONE JOINTER FIXING TOOL

BACKGROUND OF THE INVENTION

1. Field of the Invention

The present invention relates to a bone jointer in order to carry out junction, for example, of a fractured part at a neck of femur. More particularly, the present invention relates to that in which junction of the bone may be carried out corresponding to various types of fracture by easily obtaining the strong fixed state.

The present invention also relates to a bone jointer fixing tool used when the bone jointer is used in order to carry out junction, for example, of a fractured part of the neck of femur. More particularly, the present invention also relates to that in which the bone jointer may easily and accurately be fixed corresponding to various types of fracture.

2. Description of the Related Art

There is an example of bone jointer disclosed in the prior art, such as the Japanese utility model registration No. 3044923, which is owned by the applicant of the present invention, as illustrated in FIG. 20.

FIG. 20 illustrates the state of fracture at a neck 300a of a femur 300, as well as the structure of a bone jointer in order to carry out junction of such a fracture part, which is shown by letter A.

There is a tube plate 301 placed along the side of the femur 300. A hemispherical shape of receiver 303 is formed at the top of the tube plate 301 as shown in FIG. 20. The receiver 303 has a penetration hole 305.

A hole is formed in the femur 300, through which a tube 307 is placed, thus the tube 307 is positioned inside the receiver 303. The tube 307 has a hemispherical shape of head 309 and is movably engaged with the receiver 303 via the head 309. The tube 307 has a hollow part 311, and an internal thread 313 is formed on the inner periphery of the head 309. The receiver 303 has a matt (i.e. slightly rough or sandy) surface, and the same is true to the surface of the head 309. Accordingly, when the head 309 is received by the receiver 303, a large frictional force as well as a large fixing force may be obtained.

There is a lag screw 315 provided with a shaft 317 of which cross sectional shape is hexagon. The shaft 317 has an external thread 319 formed at the top thereof, and also has an internal thread 320 formed on the inner periphery of the basement (that is, the lower side of FIG. 20) thereof. With this structure, a hole has been formed in advance from the femur 300 toward a bone head 300b, and the lag screw 315 is inserted in this hole. Then the lag screw 315 becomes engaged with an internal thread provided on the hole of the bone head 300b.

There is also a set screw 321 provided on the outer periphery of the receiver 303 of the tube plate 301. The set screw 321 has an external thread 323 which is to be engaged with the internal thread 313 of the tube 307. The compression screw 325 has an external thread 327 to be engaged with the internal thread 320 of the lag screw 315.

Further, the tube plate 301 has a plurality of penetration holes 331 through which the cortical bone screws 329 each serving as the fixing screw may respectively be penetrated. The tube plate 301 also has another penetration hole 335 into which a canulated screw 333 may be penetrated.

According to this structure, when there is a fracture at the neck 300a of the femur 300, for example, a predetermined depth of hole is first drilled from the femur 300 toward the bone head 300b, then the internal thread is cut in the bone head 300b. After that, the lag screw 315 is inserted to be engaged with the cut internal thread of the bone head 300b, and the tube 307 is also inserted therein. In such a state, the basement of the lag screw 315 is inserted in the hollow part 311 inside the tube 307.

The tube plate 301 has been placed along the side of the femur 300, and the set screw 321 is inserted in the penetration hole 305 of the receiver 303 of the tube plate 301. Thus the set screw 321 is engaged with the internal thread 313 of the head 309 of the tube 307 in order to fix the tube 307 on the tube plate 301. Then the compression screw 325 is inserted in the set screw 321, so that the compression screw 325 may be engaged with the internal thread 320 provided inside the basement of the lag screw 315. Accordingly, the lag screw 315, as well as the bone head 300b, will be drew toward the femur 300 in order to apply the pressure to the fracture part A. Then the plurality of the cortical bone screws 329 and the canulated screw 333 are screwed into the femur 300 from the outside of the tube plate 301 in order to fix the fracture part.

However, the prior art has the following disadvantageous point.

According to the prior art as above discussed, both the head 309 of the tube 307 and the receiver 303 of the tube plate 301 are hemispherical shapes, so that the tube 307 may move in all directions relative to the tube plate 301, in order to cope with any directional force of the tube 307 as well as the lag screw 315 applied to the tube plate 301.

However, the connection of the set screw 321 to the tube 307 is difficult, and even after the set screw 321 has been connected to the tube 307, there may occur another problem of the improper positioning due to a clearance between the set screw 321 and the penetration hole 305 of the tube plate 301. This will cause the inaccurate positioning as well as the weakened fixing force.

Further, when this type of bone jointer is fixed, there has been a demand that the fixing of the jointer should be carried out easily and more accurately.

SUMMARY OF THE INVENTION

It is an object of the present invention to provide a bone jointer by which a facile junction of the bone is accomplished, and the accurate positioning with the strong fixing force is surely be obtained.

Further, it is also an object of the present invention to provide a bone jointer fixing tool by which the facile fixing of the bone jointer can be accomplished.

To achieve the object mentioned above, according to claim 1 of the present invention, there is provided a bone jointer comprising, a lag screw inserted from a bone at one side as an object of junction and is engaged with a bone at the other side; a tube plate placed along the bone at one side and provided with a receiving part having a penetration hole; a tube positioned between the lag screw and the tube plate, into which a base of the lag screw is inserted, and provided with a head with which an inner periphery of the receiving part of the tube plate is movably engaged; a set screw inserted from outside of the tube plate and engaged with an inner periphery of the tube in order to fix the tube on the tube plate; a compression screw inserted from outside of the tube plate, penetrating inside the set screw, and engaged with the lag screw, thereby the lag screw as well as the bone on the other side are drew toward the bone at one end; and a washer inserted in a position between the set screw and an outer periphery of the receiving part of the tube plate, rotating during engagement of the set screw with the head of the tube, until the washer stops at a stablest position.

According to claim 2, there is provided the bone jointer of claim 1, wherein the washer having a penetration hole drilled at a deviated position from the center of a hemisphere shape of the washer, with a top of the hemisphere shape being cut away.

According to claim 3, there is provided the bone jointer of claim 1, wherein a rim of the penetration hole of the tube plate on the side of the washer is formed in an arc shape, and the rim on the side of the head of the tube is also formed in an arc shape, having a linear penetration part between the two rims in arc shapes, thereby contact of the washer with the head of the tube during setting is prevented.

According to claim 4, there is provided the bone jointer of claim 1, wherein a thread of the lag screw is sawlike shape having a tapping function.

According to claim 5, there is provided the bone jointer of claim 1, wherein a surface of the head of the tube and a surface of the receiving part of the tube plate facing the tube are matt (i.e. slightly rough and sandy) finished.

With this structure, the washer is positioned between the set screw and the tube plate, and when the set screw is screwed to be engaged with the tube, the washer is automatically positioned at the stablest position for fixing the screw, thus the fixing of the screw may be carried out by maintaining this stablest position of the washer. Accordingly, in whichever direction the lag screw and the tube are placed against the tube plate, since the washer automatically positioned at the stablest position through rotation corresponding to the screwing rotation of the lag screw, the strong fixing state may surely be obtained through a remarkable facile procedure.

According to the bone jointer according to the present invention, when the set screw is engaged with the internal thread of the head of the tube, the washer effectively serves to obtain the stable fixed state of the set screw. This is because, when the washer rotates corresponding to the directional force of the lag screw and the tube against the tube plate, the washer automatically finds the stablest position for fixing the set screw, and the rotation of the washer stops at that point. Accordingly, as compared with the prior art, the junction procedure may remarkably be facilitated, and after the set screw is fastened, the loosening thereof may effectively be prevented.

Further, according to claim 6, there is provided a bone jointer fixing tool comprising, a plate placed along a bone at one side as an object of junction and provided with a receiving part having a penetration hole; a screw placed closer to the bone at one side than the receiving part, having a shaft inserted in the penetration hole of the receiving part, also having a head in slidable contact with an inner periphery of the penetration hole of the receiving part, and having a penetration hole through which a drill is penetrated; a washer placed farther to the bone at one side than the receiving part, of which outer peripheral surface being in slidable contact with an inner peripheral surface of the penetration hole of the receiving part; and a fastening part placed farther to the receiving part than the washer, being engaged with the screw, and having a penetration hole through which the drill is penetrated, wherein, while the screw is engaged with the fastening part in arbitrary direction, the washer rotates and then stops at the stablest position, thereby the screw and the fastening part are engaged with each other by maintaining the arbitrary direction.

According to claim 7, there is provided the bone jointer fixing tool of claim 6, wherein the washer having a penetration hole drilled at a deviated position from the center of a hemisphere shape of the washer, with a top of the hemisphere shape being cut away.

According to claim 8, there is provided the bone jointer fixing tool of claim 6, wherein the washer is provided with a protrusive pin for rotative control of the washer.

According to claim 9, there is provided the bone jointer fixing tool of claim 6, wherein the receiving part of the plate has a pair of sphere shape of hollow parts on both sides, and the penetration hole is formed by opening a hole connecting the hollow parts to each other.

According to claim 10, there is provided the bone jointer fixing tool of claim 6, wherein the plate has a plate part provided with the receiving part at an end top of the plate part, and a cross sectional shape of the plate part is formed as slightly hollow shape, and a pair of stoppers in a sawlike shape is formed at each edge of the plate part.

With this structure, according to the bone jointer fixing tool of the present invention, the plate is first placed along the side of the bone to be jointed (whether the plate is fixed or not may be determined arbitrary). The screw is placed on the receiving part of the plate at the position closer to the bone to be jointed, and the washer as well as the fastening part are positioned on the other side of the screw. Then the screw are lightly engaged with the fastening part, and are rotated in order to be in the most appropriate and desired direction. This rotation can be accomplished since the head of the screw is in slidable contact with the inner peripheral surface of the penetration hole of the receiving part. When the most appropriate (i.e. the stablest) position is determined, the screw is strongly engaged with the fastening part. In such a state, the outer peripheral surface of the washer rotates through in slidable contact with the inner peripheral surface of the receiving part, and then stops at the stablest position. After that, the screw is strongly cramped by maintaining such a state by the fastening part, thereby the screw and the fastening part may be strongly fixed at the position in the desired direction. Since the washer is positioned at the stablest position after completion of rotation, the direction of the fixed screw and the fastening part may not easily be changed.

Then the drill is inserted in the penetration holes of the fastening part and the screw, and the hole is further drilled. Eventually, the hole and the drill may be used as the guide for fixing of a bone jointer such as that disclosed in Japanese patent application No. Hei 10-129371.

According to the bone jointer fixing tool of the present invention, first, the facile and more accurate fixing of the bone jointer can be accomplished. For the purpose of fixing the bone jointer at the accurate position, it is necessary to determine the direction of the drill carefully and accurately. In this connection, when the screw is lightly cramped by the fastening part, it is possible to move the screw as well as the fastening part in any direction. Then, by strongly cramping the screw by the fastening part, such an accurate direction of the drill may easily be determined. In addition, once the direction of the drill is determined, such a direction may not easily be changed due to existence of the washer.

BRIEF DESCRIPTION OF THE DRAWINGS

The invention will be described below in detail with reference to the accompanying drawings, in which:

FIG. 9 is an exploded perspective view of the bone jointer fixing tool according to the fourth embodiment of the present invention;

FIG. 12 is a front sectional view showing the order of manufacturing process of a washer used as an element part of the bone jointer fixing tool according to the fourth embodiment of the present invention;

DETAILED DESCRIPTION OF THE INVENTION

First Embodiment

A first embodiment of the present invention will now be described with reference to FIGS. 1 through 5.

Figure 1:
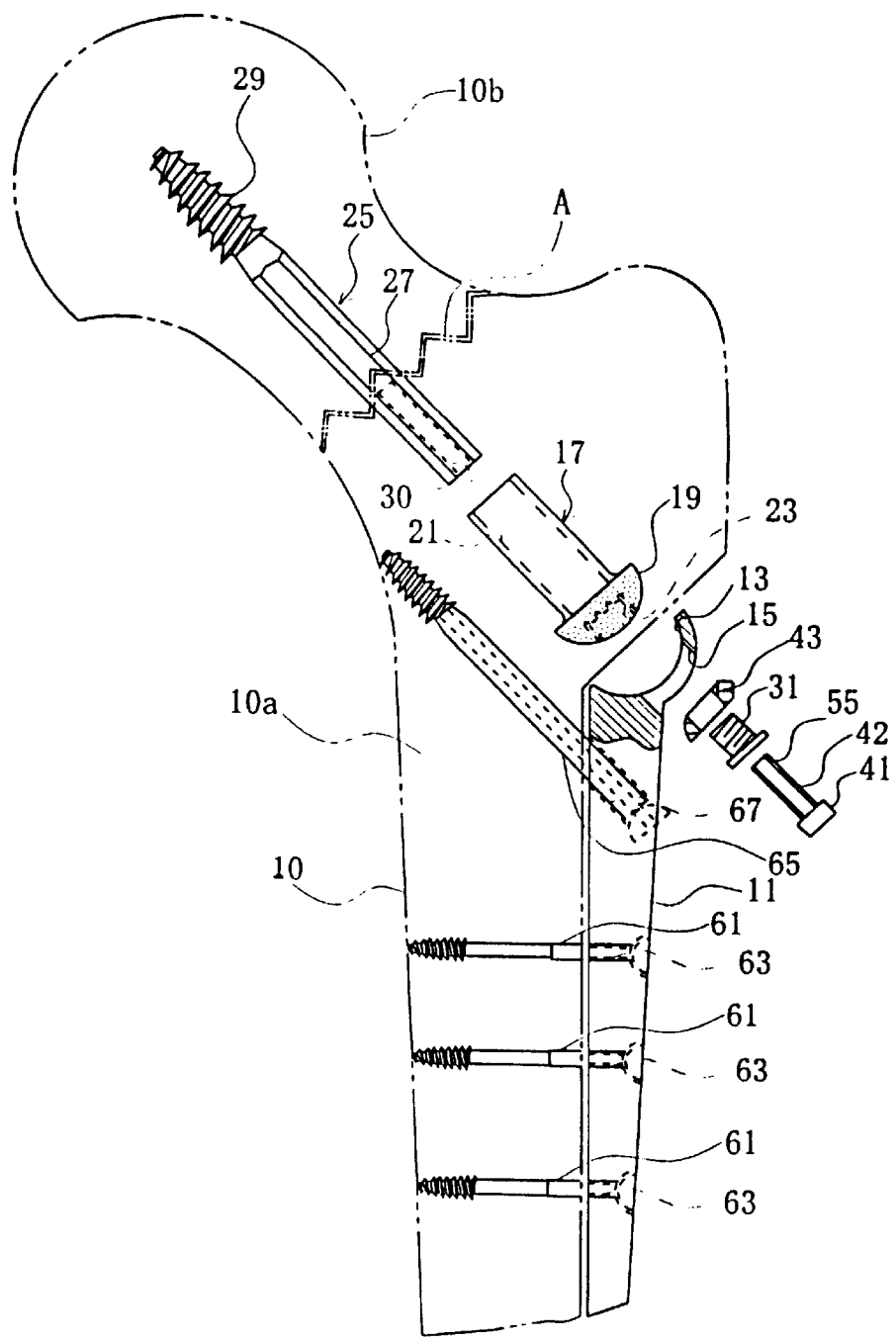
FIG. 1 is a view performing a junction of a fracture part of a neck of a femur by using a bone jointer according to a first embodiment of the present invention.

FIG. 1 illustrates the state of fracture at a neck 10a of a femur 10, as well as the structure of a bone jointer according to the present embodiment in order to carry out junction of such a fracture part, which is shown by letter A.

There is a tube plate 11 placed along the side of the femur 10. A hemispherical shape of receiver 13 is formed at the top of the tube plate 11 as shown in FIG. 1. The receiver 13 has a penetration hole 15.

A hole is formed in the femur 10, through which a tube 17 is placed, thus the tube 17 is positioned inside the receiver 13. The tube 17 has a hemispherical shape of head 19 and is movably engaged with the receiver 13 via the head 19. The tube 17 has a hollow part 21, and an internal thread 23 is formed on the inner periphery of the head 19. The receiver 13 has a matt (i.e. slightly rough or sandy) surface, and the same is true to the surface of the head 19. Accordingly, when the head 19 is received by the receiver 13, a large frictional force as well as a large fixing force may be obtained.

There is a lag screw 25 provided with a shaft 27 of which cross sectional shape is hexagon. The shaft 27 has an external thread 29 formed at the top thereof, and also has an internal thread 30 formed on the inner periphery of the basement (that is, the lower side of FIG. 1) thereof. With this structure, a hole has been formed in advance from the femur 10 toward a bone head 10b, and the lag screw 25 is inserted in this hole. Then the lag screw 25 becomes engaged with an internal thread provided on the hole of the bone head 10b.

Figure 5:
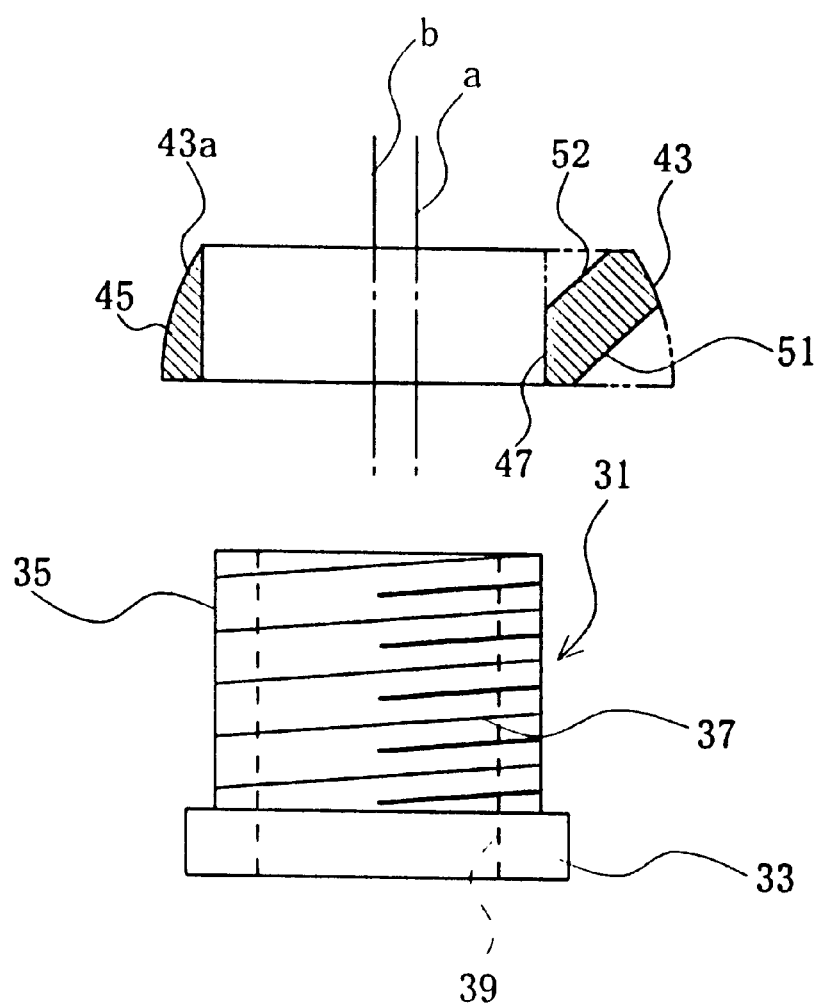
FIG. 5 is a view explaining the order of manufacturing process of the washer according to the first embodiment of the present invention.

There is also a set screw 31 provided on the outer periphery of the receiver 13 of the tube plate 11. As illustrated in FIG. 5, the set screw 31 comprises a head 33 and a shaft 35, and an external thread 37 is formed on the outer periphery of the shaft 35. The external thread 37 is to be engaged with the internal thread 23 of the head 19 of the tube 17. Further, there is a hexagonal shape of penetration hole 39 formed on the inner periphery of the shaft 35, so that a compression screw 41 may be penetrated through this penetration hole 39. The compression screw 41 has an external thread 42 to be engaged with the internal thread 30 of the lag screw 25.

FIG. 5 also shows a washer 43 which is inserted in the position between the set screw 31 and the penetration hole 15 of the tube plate 11. This washer 43 has a function that, regardless of the direction of the lag screw 25 and the tube 17 against the tube plate 11, the facile engagement of the set screw 31 with the internal thread 23 of the head 19 of the tube 17, and the stable fixed state between them, may be accomplished.

Figure 2:
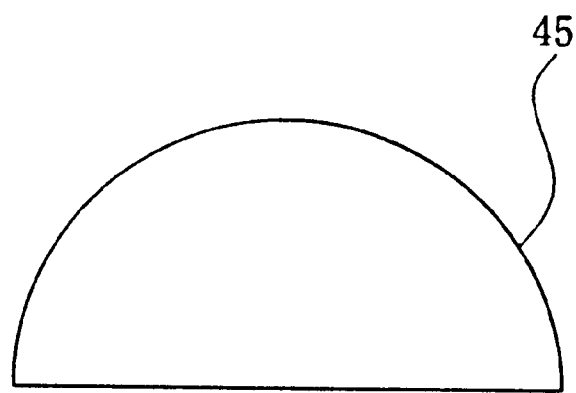
FIG. 2 is a view explaining the order of manufacturing process of a washer according to the first embodiment of the present invention.
Figure 3:
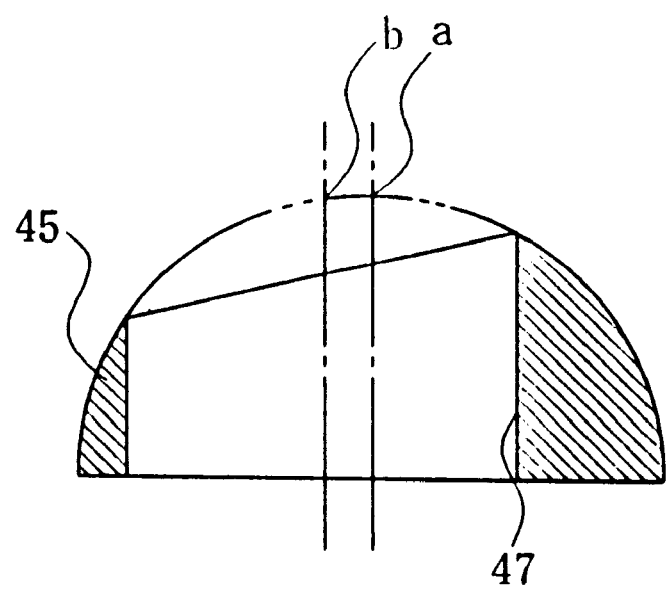
FIG. 3 is a view explaining the order of manufacturing process of the washer according to the first embodiment of the present invention.
Figure 4:
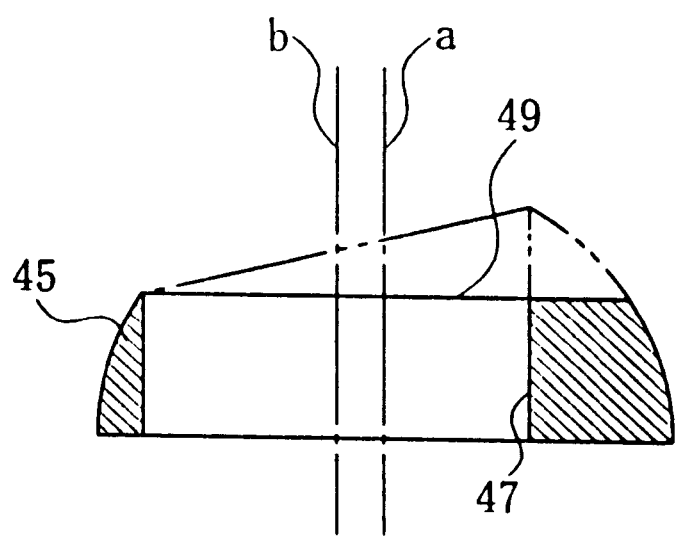
FIG. 4 is a view explaining the order of manufacturing process of the washer according to the first embodiment of the present invention.

The shape of this washer 43 will now be described with reference to FIGS. 2 through 5, according to the order of manufacturing process thereof. First, as shown in FIG. 2, a hemispherical shape of a material 45 is prepared. Then, as shown in FIG. 3, an axis b is determined at the offset position by a predetermined amount from the actual axis a, and a penetration hole 47 having a determined diameter is drilled by making the axis b as the center thereof. After that, as shown in FIG. 4, the upper part of the material 45 is cut away along a cutting line 49. Eventually, as shown in FIG. 5, a part of the material 45 is cut along a cutting line 51, and another part of the material 45 is also cut along a cutting line 52, thus the washer 43 according to the present embodiment is obtained.

With this structure, the washer 43 has an outer peripheral surface 43a which may freely move against the penetration hole 15.

Now referring back to FIG. 1, the tube plate 11 has a plurality of penetration holes 63 through which the cortical bone screws 61 each serving as the fixing screw may respectively be penetrated. The tube plate 11 also has another penetration hole 67 into which a canulated screw 65 may be penetrated.

The function of the present embodiment will be described based on the structure as above discussed.

For example, when there is a fracture at the neck 10a of the femur 10, a predetermined depth of hole is first drilled from the femur 10 toward the bone head 10b, then the internal thread is cut in the bone head 10b. After that, the lag screw 25 is inserted to be engaged with the cut internal thread of the bone head 10b, and the tube 17 is also inserted therein. In such a state, the basement of the lag screw 25 is inserted in the hollow part 21 inside the tube 17.

The tube plate 11 has been placed along the side of the femur 10, and the set screw 31 is inserted, via the washer 43, in the penetration hole 15 of the receiver 13 of the tube plate 11. Thus the set screw 31 is engaged with the internal thread 23 of the head 19 of the tube 17. At that time, the direction of the lag screw 25 and the tube 17 against the tube plate 11 may arbitrarily be determined, and in any case, as the set screw 31 is gradually screwed to become engaged with the internal thread 23, the washer 43 also rotates corresponding to the directional force of the lag screw 25 and the tube 17 against the tube plate 11. Accordingly, the rotation of the washer 43 stops at the most appropriate position at which the set screw may obtain the strongest fixing force.

Then the compression screw 41 is inserted in the set screw 31, so that the compression screw 41 may be engaged with the internal thread 30 provided inside the basement of the lag screw 25. Accordingly, the lag screw 25, as well as the bone head 10b, will be drew toward the femur 10 in order to apply the pressure to the fracture part A. Then the plurality of the cortical bone screws 61 and the canulated screw 65 are screwed into the femur 10 from the outside of the tube plate 11 in order to fix the fracture part.

According to the present embodiment, when the set screw 31 is engaged with the internal thread 23 of the head 19 of the tube 17, the washer 43 effectively serves to obtain the stable fixed state of the set screw 31. When the washer 43 rotates corresponding to the directional force of the lag screw 25 and the tube 17 against the tube plate 11, the outer peripheral surface 43a of the washer 43 also rotates through slidable contact with a rim of the penetration hole 15 of the tube plate 11. Then, through such a rotation, the outer peripheral surface 43a automatically finds the stablest position for fixing the set screw 31, and the rotation of the washer 43 stops at that point.

Accordingly, as compared with the prior art, the junction procedure may remarkably be facilitated, and after the set screw is fastened, the loosening thereof may effectively be prevented.

Second Embodiment

Figure 6:
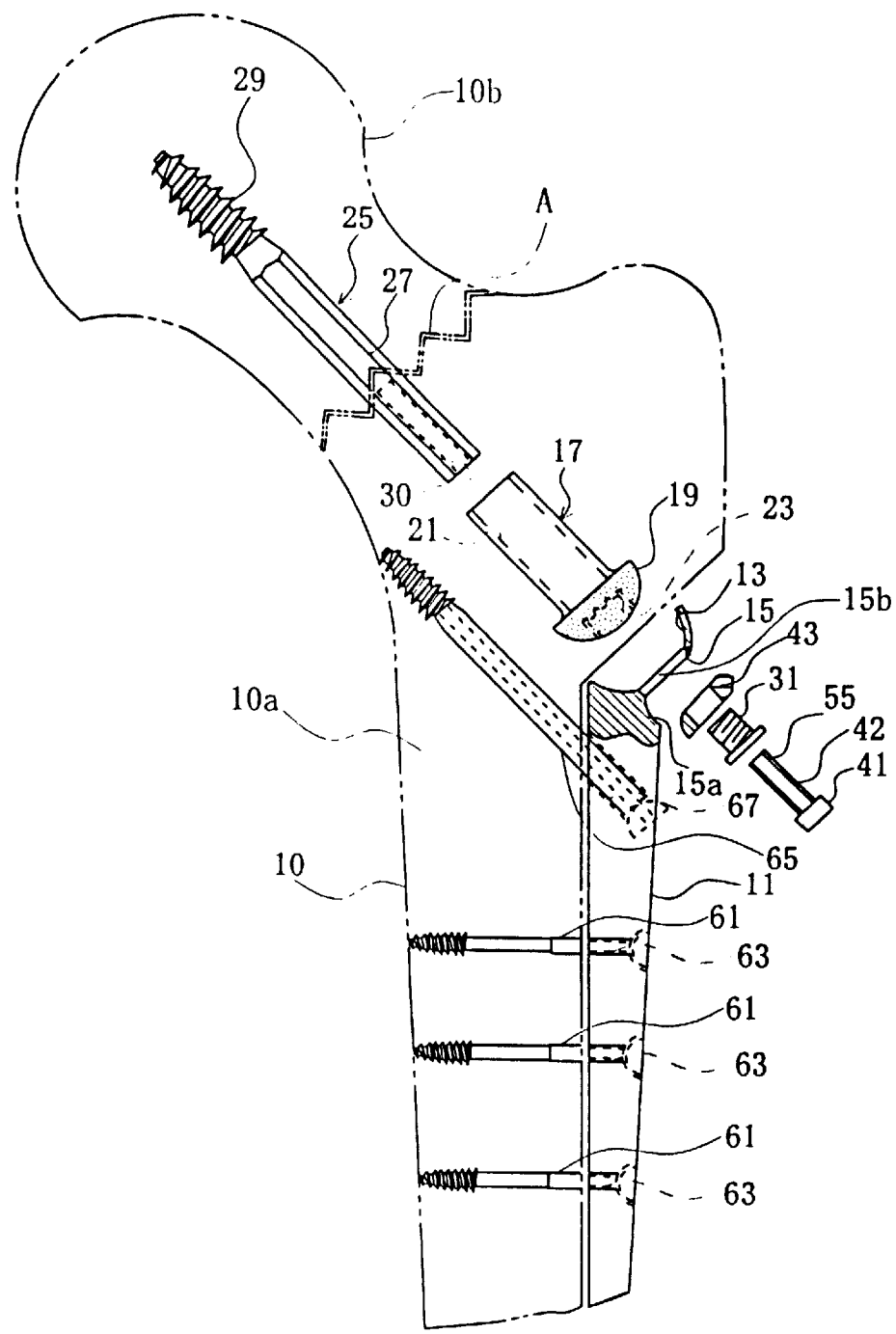
FIG. 6 is a view performing a junction of a fracture part of a neck of a femur by using a bone jointer according to a second embodiment of the present invention.

A second embodiment of the present invention will be described with reference to FIG. 6. According to the second embodiment, an arc surface 15a is provided at the penetration hole 15 of the tube plate 11, on the side facing the washer 43. Due to existence of this arc surface 15a, when the set screw 31 is screwed (i.e. during "setting"), the washer 43 will partially be accommodated in such an arc surface 15a. In other words, during setting, the protrusion (going outside) of the washer 43 by a large amount may be prevented.

When the arc surface 15a is provided, a linear shape of penetration part 15b should be provided between the arc surface 15a and the receiver 13. The penetration part 15b in the linear shape prevents the contact of the washer 43 with the head 19 of the tube 17, thereby the clearance for screwing may be obtained.

For reference, in the case of the first embodiment of the present invention, the penetration hole 15 has been formed in the linear shape, and the washer 43 becomes in contact with the rim of the penetration hole 15. Therefore the washer 43 will not be in contact with the head 19 of the tube 17.

Third Embodiment

Figure 7:
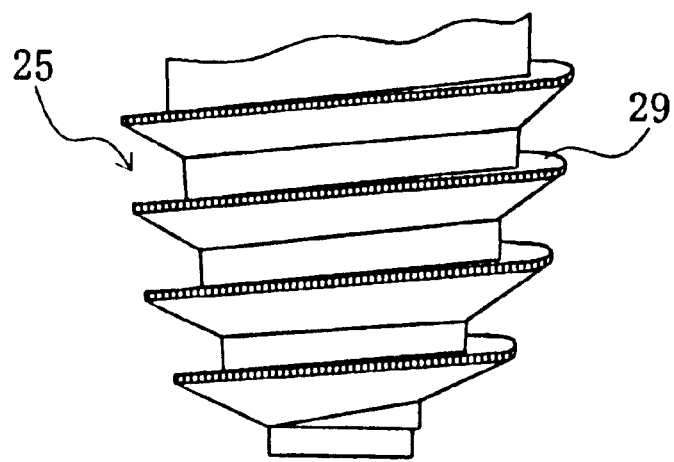
FIG. 7 is a view showing a structure of a top of a lag screw according to the third embodiment of the present invention.

A third embodiment of the present invention will be described with reference to FIG. 7. According to the third embodiment, the external thread 29 of the lag screw 25 is formed in a sawlike shape in order to be provided with a tapping function. When the bone jointer is used, the hole has been drilled in advance from the femur 10 toward the bone head 10b. Then, it is necessary to carry out the tapping in order to allow the insertion of the lag screw 25. In the third embodiment, however, since the external screw 29 of the lag screw 25 has the tapping function, the tapping can be carried out at the same time of insertion of the lag screw 25.

Fourth Embodiment

Figure 8:
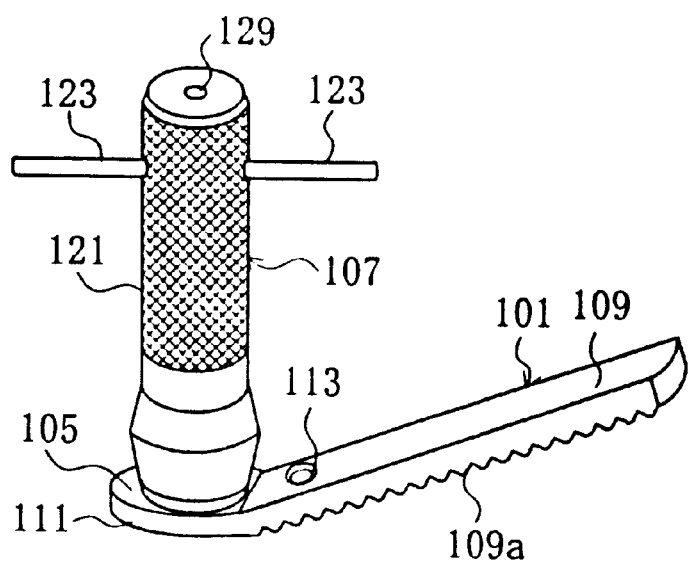
FIG. 8 is a perspective view of a bone jointer fixing tool according to a fourth embodiment of the present invention.

The fourth embodiment of the present invention will now be described with reference to FIGS. 8 through 19. As illustrated in FIGS. 8 and 9, a bone jointer fixing tool according to the present embodiment comprises, a plate 101, a screw 103, a washer 105 and a fastening tool 107.

For reference, the screw 103 is not illustrated in FIG. 8 since the screw 103 has been screwed into the fastening tool 107 through the plate 101 and the washer 105.

Figure 10:
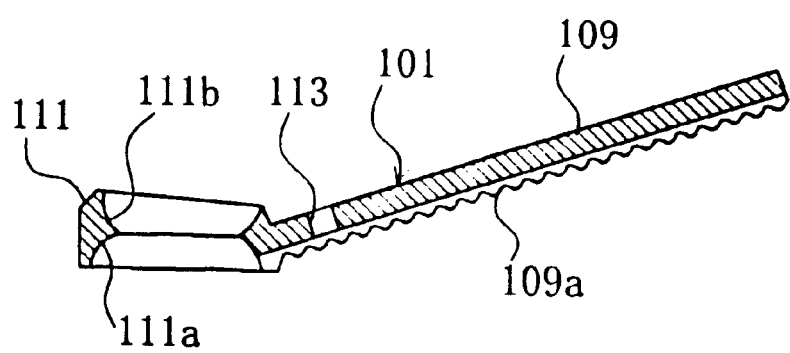
FIG. 10 is a sectional view showing a structure of a plate of the bone jointer fixing tool according to the fourth embodiment of the present invention.

As illustrated in FIGS. 8, 9 and 10, the plate 101 comprises a plate part 109 and a receiving part 111 formed at the top of the plate part 109. The cross sectional shape of the plate part 109 is slightly hollow, having sawlike shape of a stoppers 109a, 109a at the edges thereof. As illustrated in FIG. 8, the receiving part 111 is substantially formed as the ring shape, and both of the plane surfaces thereof are provided with substantially spherical shape of hollow parts 111a, 111b, respectively (see FIG. 10). Further, there is a penetration hole 113 provided at the base of the plate part 9.

The screw 103 will be discussed with reference to FIG. 9. There is a shaft 115 and a head 117, and an external thread 118 has been formed on the shaft 115. The head 117 is provided with a pair of curved surfaces 117a, 117b. Further, in regard to the whole unit comprising the shaft 115 and the head 117, there is formed a penetration hole 119 penetrated through the axis of such a whole unit.

The curved surface 117b of the head 117, and the hollow part 1111a of the receiving part 111 of the plate 101, are both finished to be the matt (slightly rough or sandy) surface.

Figure 11:
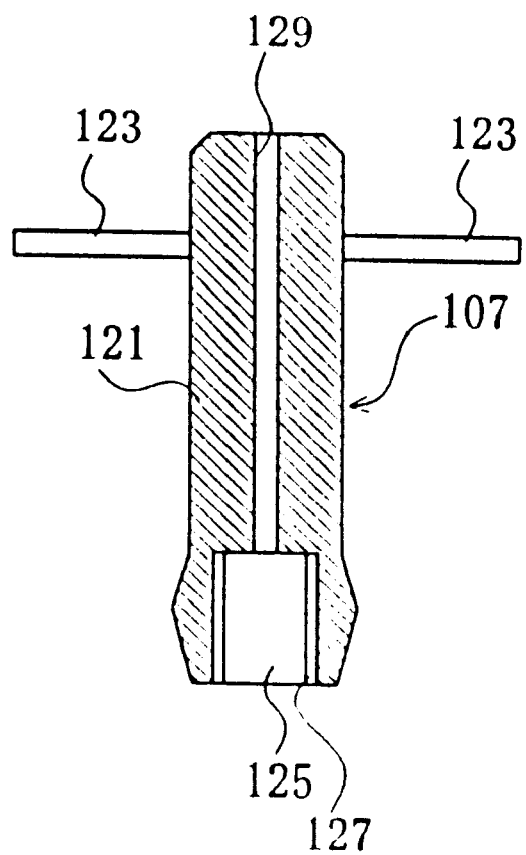
FIG. 11 is a sectional view showing a structure of a fastening tool of the bone jointer fixing tool according to the fourth embodiment of the present invention.

Now the structure of the fastening tool 107 will be discussed. There is a shaft 121, of which base is provided with a pair of handles 123, 123. Each of the handles 123, 123 is in a shape of stick and is protruding in the direction perpendicular to the axis of the shaft 121. As illustrated in FIG. 11, there is a hollow part 125 formed at the top of the shaft 121, and an internal thread 127 is formed on this hollow part 125. Thus the internal thread 127 is to be engaged with the above discussed external thread 118 of the shaft 115 of the screw 103. Further, there is a penetration hole 129 formed at the axis of the shaft 115.

Figure 13:
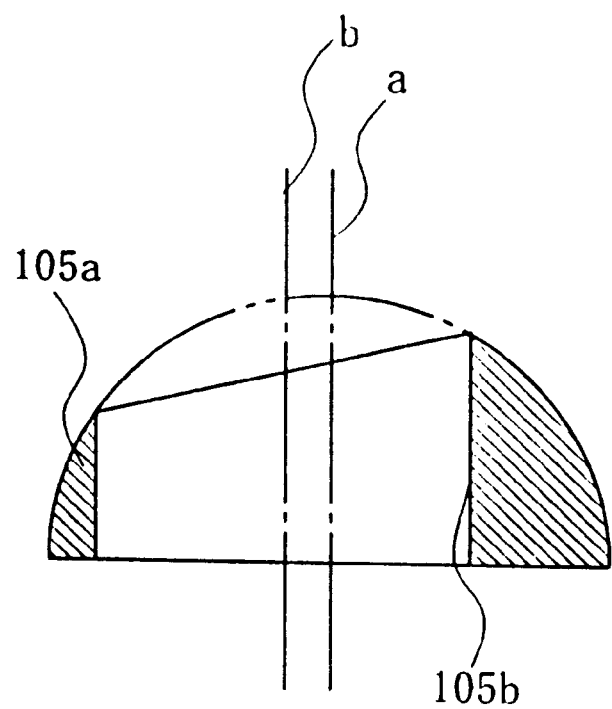
FIG. 13 is a front sectional view showing the order of manufacturing process of the washer used as the element part of the bone jointer fixing tool according to the fourth embodiment of the present invention.

The structure of the washer 105 will be described. The washer 105 is basically the same structure as the washer 43 of the first embodiment of the present invention. The shape of the washer 105 will now be described with reference to Figs. 12 through 15, according to the order of manufacturing process thereof. First, as shown in FIG. 12, a hemispherical shape of a material 105a is prepared. Then, as shown in FIG. 13, an axis b is determined at the offset position by a predetermined amount from the actual axis a, and a penetration hole 105b having a determined diameter is drilled by making the axis b as the center thereof.

Figure 14:
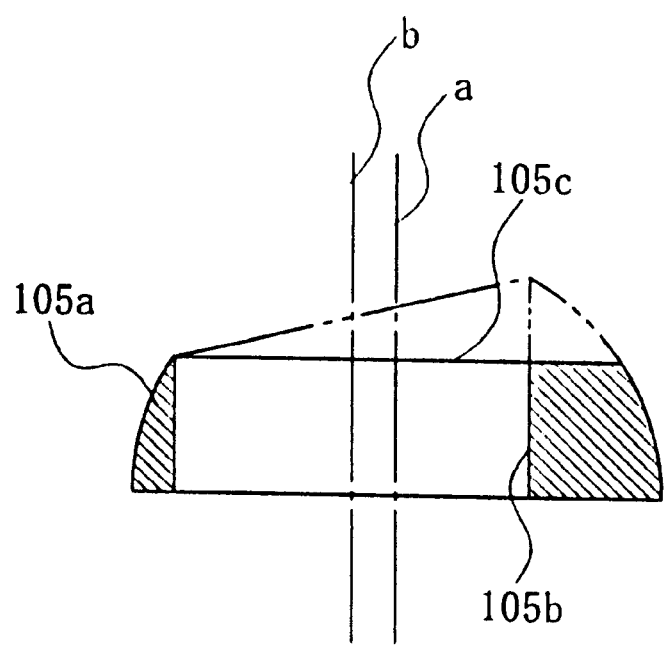
FIG. 14 is a front sectional view showing the order of manufacturing process of the washer used as the element part of the bone jointer fixing tool according to the fourth embodiment of the present invention.
Figure 15:
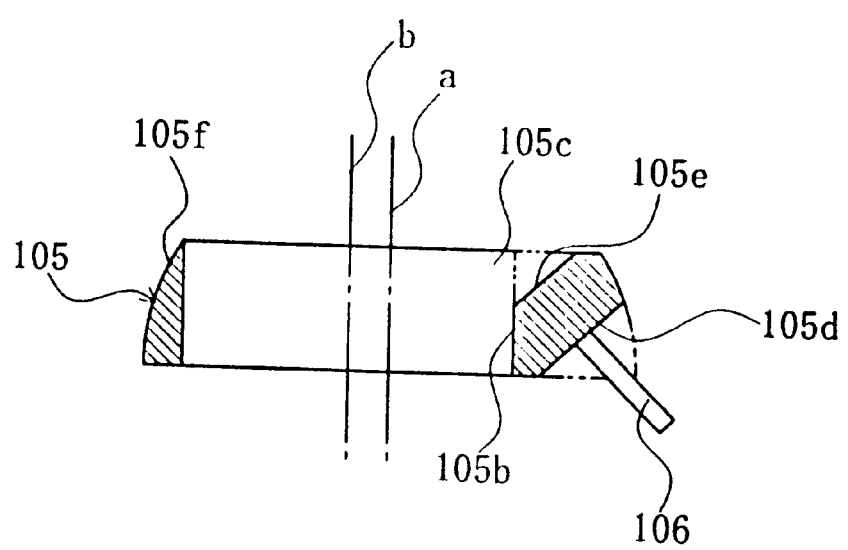
FIG. 15 is a front sectional view showing the order of manufacturing process of the washer used as the element part of the bone jointer fixing tool according to the fourth embodiment of the present invention.

After that, as shown in FIG. 14, the upper part of the material 105a is cut away along a cutting line 105c. Eventually, as shown in FIG. 15, a part of the material 105a is cut along a cutting line 105d, and another part of the material 105a is also cut along a cutting line 105e, thus the washer 105 according to the present embodiment is obtained. Accordingly, the washer 105 has an outer peripheral surface 105f which may freely move and change the position through in contact with the hollow part 111b of the receiving part 111 of the plate 101.

When the part of the material 105a is cut along the cutting line 105d, a pin 106 is provided for handling of the washer 105. This pin 106 will be used when the washer 105 should be rotated during setting.

The function of the present embodiment will be described with reference to FIGS. 16 through 19 based on the structure as above discussed.

Figure 16:
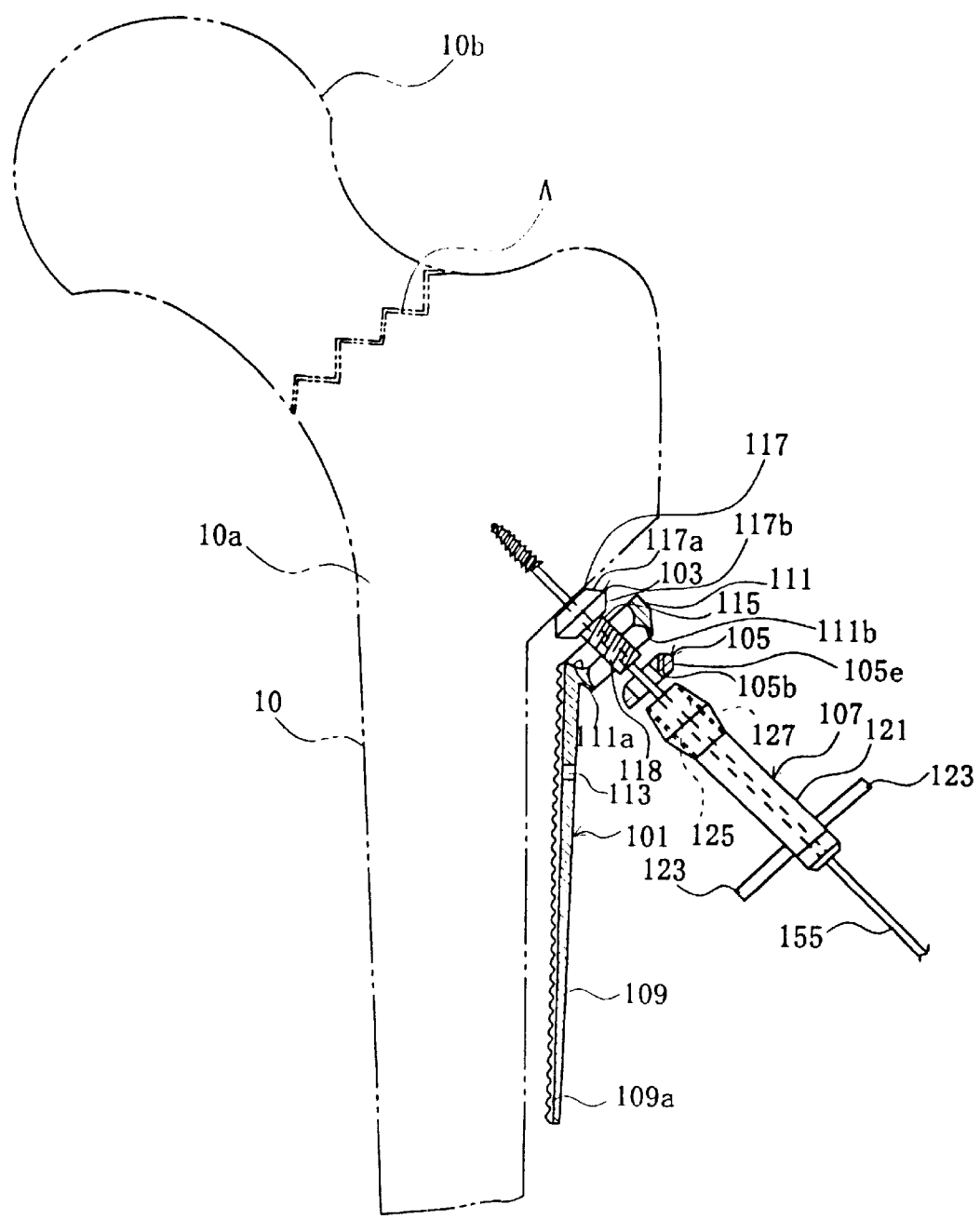
FIG. 16 is a side sectional view showing the order of fixing of the bone jointer by using the bone jointer fixing tool according to the fourth embodiment of the present invention.

As illustrated in FIG. 16, the following explanation relates to the case in which a fracture occurs at the neck 10a of the femur 10, and the junction thereof should be carried out by using the bone jointer according to the first embodiment of the present invention. The bone jointer fixing tool according to the present embodiment shall be used for fixing of such a bone jointer of the first embodiment.

For reference, the fracture part is shown by letter A in FIG. 16.

Figure 17:
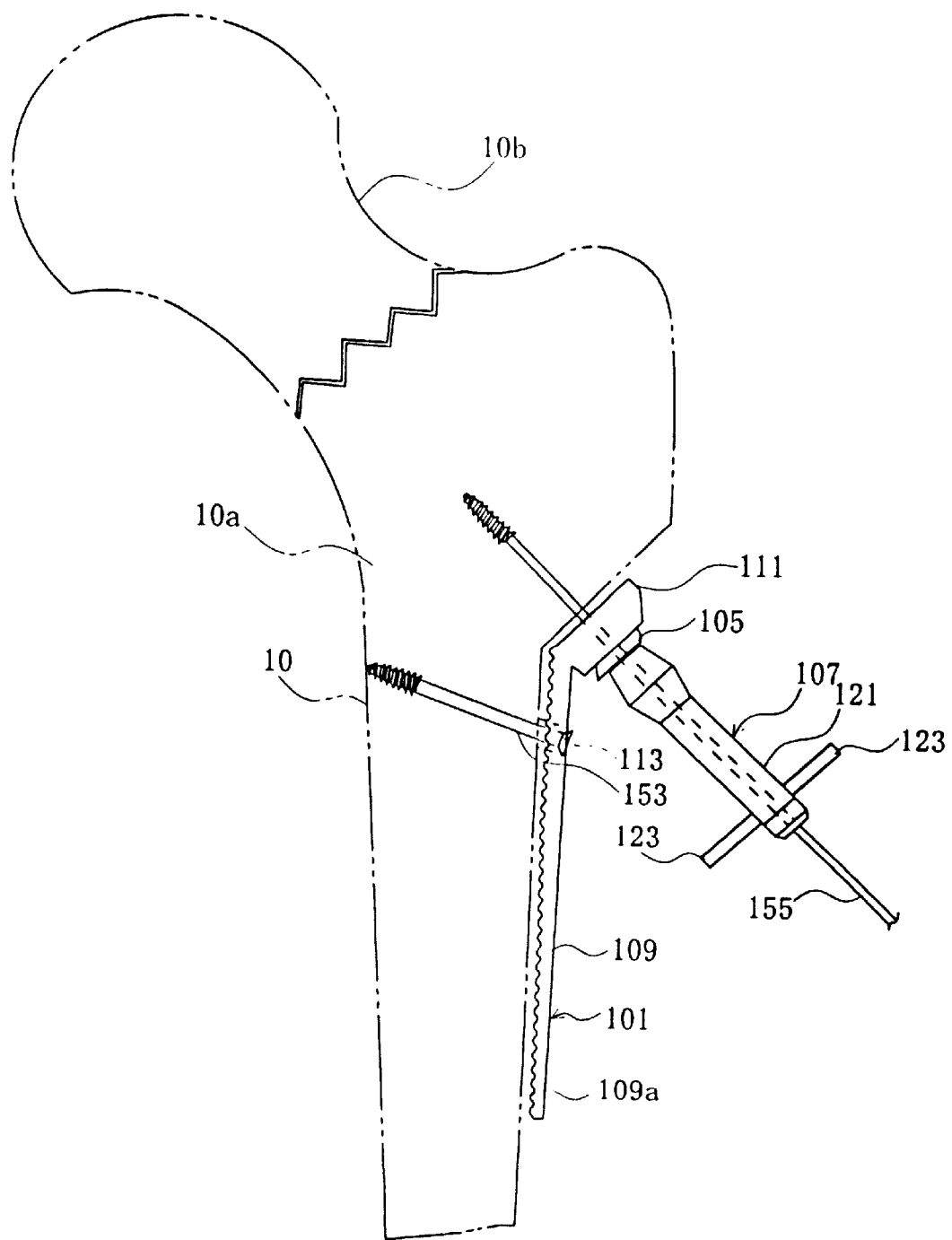
FIG. 17 is a side sectional view showing the order of fixing of the bone jointer by using the bone jointer fixing tool according to the fourth embodiment of the present invention.

First, as illustrated in FIG. 17, the plate 101 is placed along the side of the femur 10, and a cortical bone screw 153 is screwed and fixed in the femur 10 via the penetration hole 113.

Since the plate 101 is provided with the stoppers 109a, 109a, by simple pressing the plate 101 against the femur 10, the position of the plate 101 may not be moved easily. Thus the provisional fixing of the plate 101 is not required.

At that time, as shown in FIG. 16, the screw 103 has been placed in advance on the hollow part 111 of the receiving part 111 of the plate 101. Further, the shaft 115 of the screw 103 is inserted in the washer 105, and is lightly cramped by the fastening tool 107 (see FIG. 17).

In this state as shown in FIG. 17, the screw 103 has not been strongly cramped by the fastening tool 107, thus, the screw 103, the washer 105 and the fastening tool 107 all may freely move in any direction against the receiving part 111 of the plate 101. That is, the curved surface 117b of the head 117 of the screw 103 is in movable contact with the hollow part 111a of the receiving part 111, thereby the rotation of the screw 103 as well as the fastening tool 121 may be made.

Then a drill 155 is inserted in the penetration hole 129 of the fastening tool 107 as well as in the penetration hole 119 of the screw 103. In such a state, an image of the fracture part and the adjacent part thereto are monitored, for example, by an x-ray photographing, thereby the direction of the drilling by the drill 155 is determined.

At that time, the pin 106 provided on the washer 105 can be used in order to move the washer 105 in any direction by a proper amount, thereby the direction and angle of the screw 103, the fastening tool 107 and the drill 155 may be adjusted.

For reference, the x-ray photographing shall ordinarily be made at least from two different photographing positions, it will be possible to determine the accurate drilling direction by monitoring those x-ray photographs.

When the direction of drilling by the drill 155 is determined, the fastening tool 107 is strongly cramped in order to fix the screw 103, thereby the drilling direction of the drill 155 is also fixed with strong stability. At that time, the washer 105 effectively serves to surely fix the screw 103 in the desired direction. That is, the outer peripheral surface 105f of the washer 105 rotates through slidable contact with the hollow part 111b of the receiving part 111, and stops at the most appropriate and stablest position for fixing the screw 103. Then the fastening tool 107 is strongly cramped in order to fix the screw 103, thereby the screw 103, the fastening tool 107 as well as the drill 155 are strongly fixed all in a state of the desired direction. Further, since the washer 105 is positioned at the stablest position, the position and the direction of the fixed screw 103 as well as the fastening tool 107 may not be changed easily. The substantial direction of the drill 155 may be recognized by the position of the pin 106 of the washer 105.

As the drilling direction of the drill 155 has been determined, the drill 155 is driven by an unillustrated driving means, thus the drilling can be carried out in the desired direction.

Figure 18:
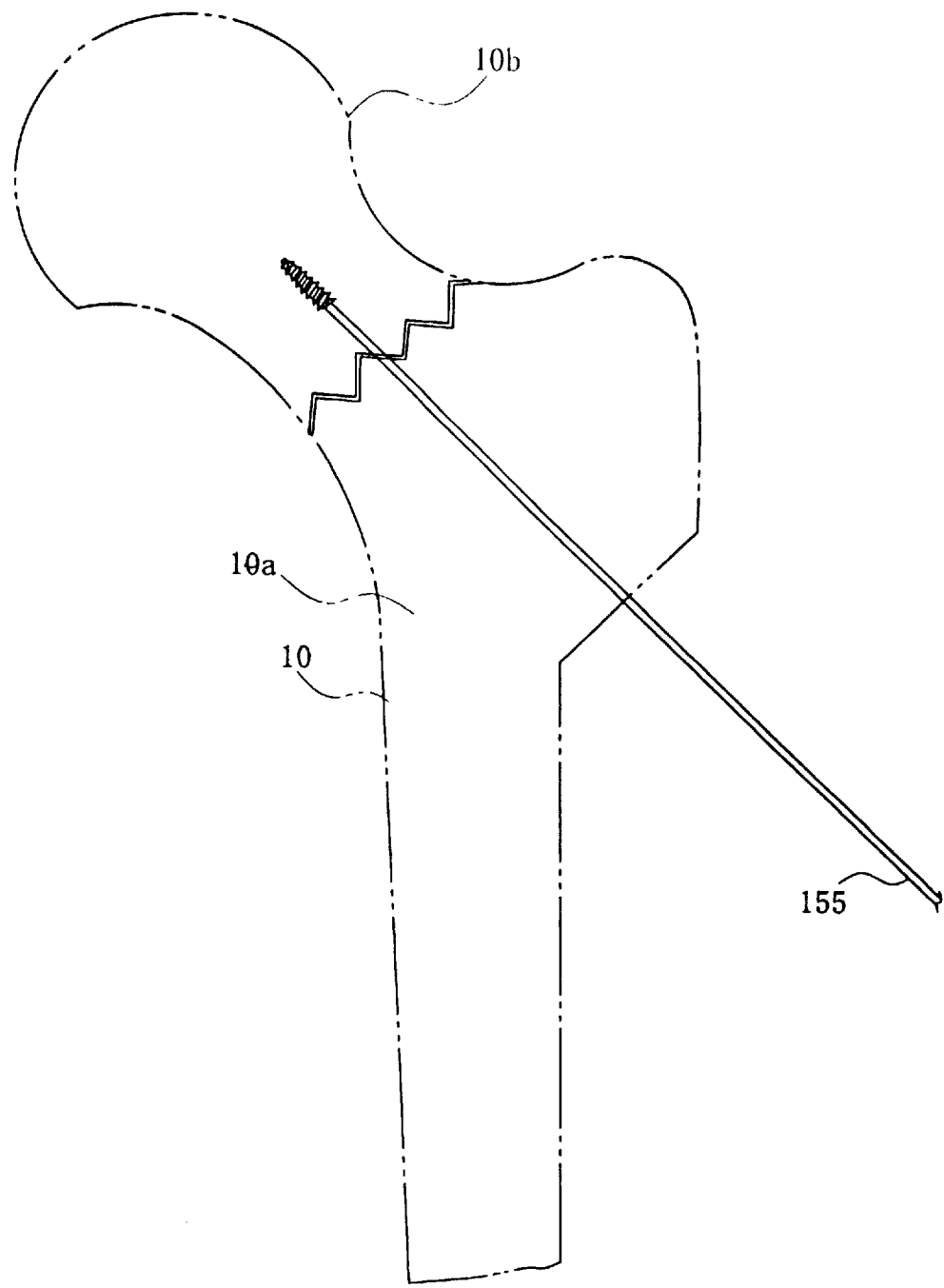
FIG. 18 is a side sectional view showing the order of fixing of the bone jointer by using the bone jointer fixing tool according to the fourth embodiment of the present invention.

After completion of drilling by the drill 155, as illustrated in FIG. 18, the whole unit of the bone jointer fixing tool other than the drill 155 is removed.

Figure 19:
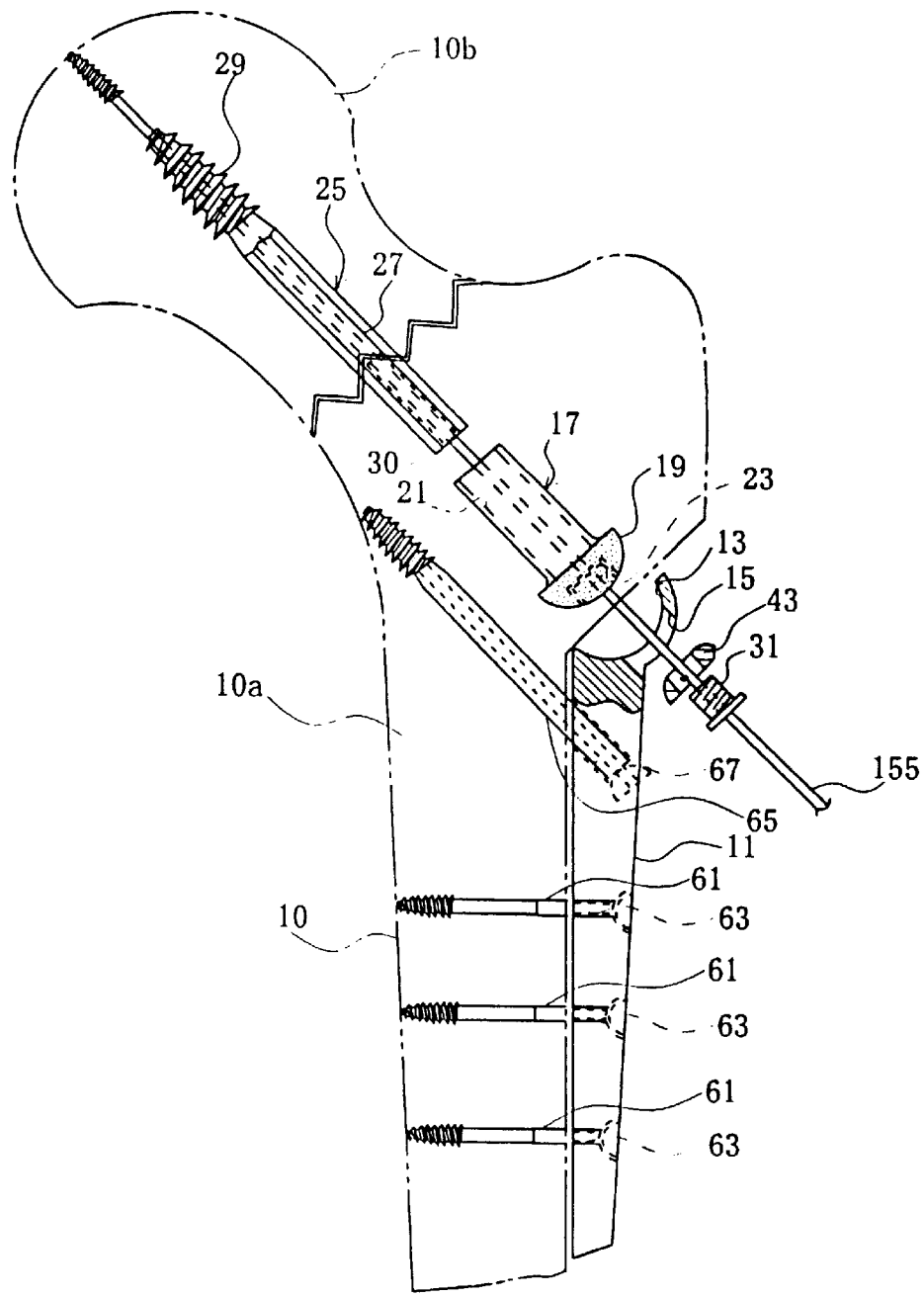
FIG. 19 is a side sectional view showing the order of fixing of the bone jointer by using the bone jointer fixing tool according to the fourth embodiment of the present invention.
Figure 20:
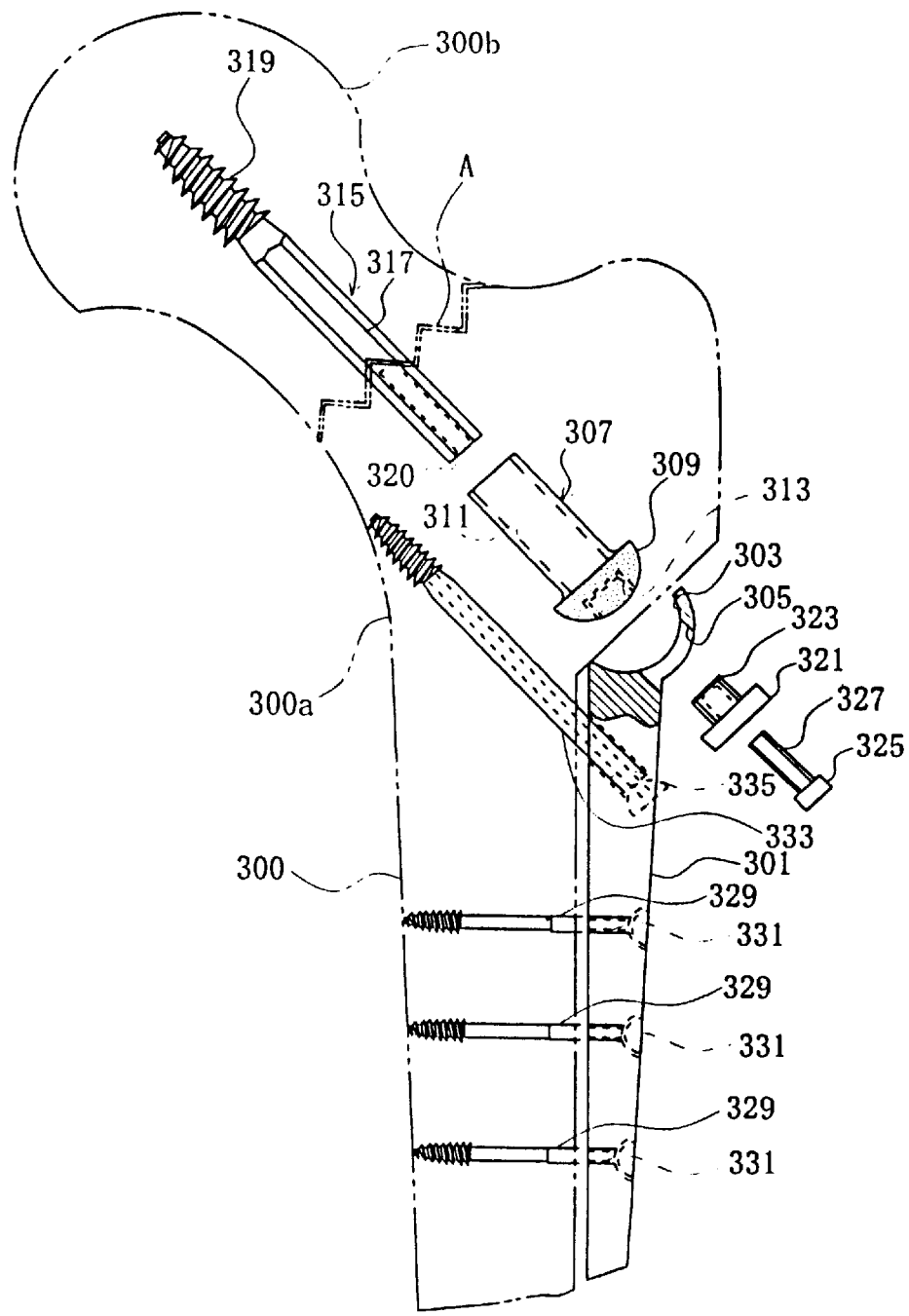
FIG. 20 is a side sectional view showing a structure of a bone jointer according to a prior art.

Then, as illustrated in FIG. 19, the bone jointer according to the first embodiment of the present invention is attached to the femur 10 by using the drill 155 as the guide. That is, the drill 155 is first used as the guide of drilling for insertion of the bone jointer by an unillustrated drilling tool. Then an unillustrated tapping tool is used for tapping (i.e. forming of an internal thread), with which the external thread 29 of the lag screw 25 is engaged. Eventually, the lag screw 25 and the tube 17 are attached to the femur 10.

When the external thread 29 of the lag screw 25 is provided with the tap function as described in the third embodiment of the present invention, the above discussed tapping procedure is not required.

The compression screw 41 shall be attached after the drill 155 is removed.

The present embodiment has the following merits.

First, the facile and more accurate fixing of the bone jointer can be accomplished. For the purpose of fixing the bone jointer at the accurate position, it is necessary to determine the direction of the drill 155 carefully and accurately. According to the present embodiment, when the screw 103 is lightly cramped by the fastening tool 107, it is possible to move the screw 103 as well as the fastening tool 107 in any direction. Then, by strongly cramping the screw 103 by the fastening tool 107, such an accurate direction of the drill 155 may easily be determined. In addition, once the direction of the drill 155 is determined, such a direction may not easily be changed due to existence of the washer 105. In the present embodiment, when the screw 103 is cramped by the fastening tool 107, the washer 105 rotates corresponding to the rotation of the screw 103. Then, through such a rotation, the washer 105 automatically finds the stablest position for fixing the screw 103, and the rotation of the washer 105 stops at that point. Thus the accurate position and direction of the drill 155 can easily be determined and maintained.

After completion of drilling by the drill 155 maintaining the accurate position and direction, the drill 155 may serve as the guide for further drilling and tapping. Then, the drill 155 may further serve as the guide of the bone jointer. Accordingly, since the direction of the bone jointer has already been determined by the drill 155, the facile fixing of the bone jointer can be accomplished.

The present embodiment is not limited to the elements as described above. For example, as for the relation between the outer peripheral surface 105e of the washer 105 and the hollow part 111b of the receiving part 111 of the plate 101, it is sufficient as long as the washer 105 may freely rotate in any direction corresponding to the screw 103 and the fastening tool 107 until stopping at the most appropriate and stablest position.

What is claimed is:

1. A bone jointer comprising:

a lag screw inserted from a bone at one side as an object of junction and is engaged with a bone at the other side;

a tube plate placed along said bone at one side and provided with a receiving part having a penetration hole;

a tube positioned between said lag screw and said tube plate, into which a base of said lag screw is inserted, and provided with a head with which an inner periphery of said receiving part of said tube plate is movably engaged;

a set screw inserted from outside of said tube plate and engaged with an inner periphery of said tube in order to fix said tube on said tube plate;

a compression screw inserted from outside of said tube plate, penetrating inside said set screw, and engaged with said lag screw, thereby said lag screw as well as said bone on the other side are drew toward said bone at one end; and a washer inserted in a position between said set screw and an outer periphery of said receiving part of said tube plate, rotating during engagement of said set screw with said head of said tube, until said washer stops at a stablest position.

2. The bone jointer as claimed in claim 1, wherein said washer having a penetration hole drilled at a deviated position from the center of a hemisphere shape of said washer, with a top of said hemisphere shape being cut away.

3. The bone jointer as claimed in claim 1, wherein a rim of said penetration hole of said tube plate on the side of said washer is formed in an arc shape, and said rim on the side of said head of said tube is also formed in an arc shape, having a linear penetration part between said two rims in arc shapes, thereby contact of said washer with said head of said tube during setting is prevented.

4. The bone jointer as claimed in claim 1, wherein a thread of said lag screw is sawlike shape having a tapping function.

5. The bone jointer as claimed in claim 1, wherein a surface of said head of said tube and a surface of said receiving part of said tube plate facing said tube are both matt (i.e. slightly rough and sandy) finished.

* * * * *